US00PP36314P2

(12) United States Plant Patent
Danziger

(10) Patent No.: US PP36,314 P2
(45) Date of Patent: Dec. 10, 2024

(54) ***GAURA* PLANT NAMED 'DGAUDARIP'**

(50) Latin Name: *Gaura lindheimeri*
Varietal Denomination: DGAUDARIP

(71) Applicant: Danziger 'DAN' Flower Farm, Beit Dagan (IL)

(72) Inventor: Gavriel Danziger, Beit Dagan (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 18/408,785

(22) Filed: Jan. 10, 2024

(51) Int. Cl.
*A01H 6/00* (2018.01)
*A01H 5/02* (2018.01)

(52) U.S. Cl.
USPC ..... Plt./432

(58) Field of Classification Search
USPC ..... Plt./432
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Gaura* plant named 'DGAUDARIP' is disclosed, characterized by a semi-upright habit, and very good branching. Plants produce abundant, deep pink colored flowers and begin to bloom carly, from spring to summer. The new cultivar is a *Gaura,* normally produced as an outdoor garden or container plant.

2 Drawing Sheets

Figure 1:
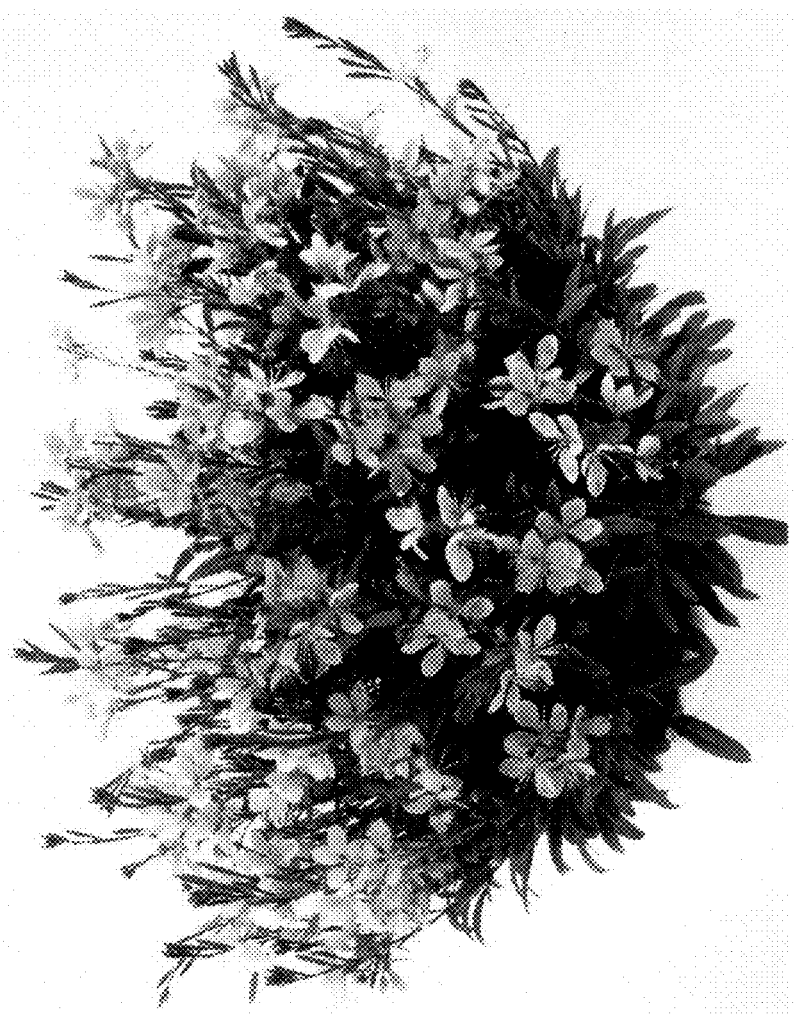

Latin name of the genus and species: *Gaura lindheimeri.*
Cultivar denomination: 'DGAUDARIP'.

BACKGROUND OF THE INVENTION

The new *Gaura* cultivar is a product of a planned breeding program conducted by the inventor, Gavriel Danziger in Moshav Mishmar Hashiva, Israel. The objective of the breeding program was to produce new *Gaura* varieties. The cross resulting in this new cultivar was made during June of 2018.

The seed parent is the unpatented, proprietary *Gaura* cultivar referred to as 'GO-15-264'. The pollen parent is the unpatented, proprietary *Gaura* cultivar referred to as 'GO-14-240'. The new cultivar was discovered in November of 2019 by the inventor in a group of seedlings resulting from the parental crossing, in a greenhouse in Moshav Mishmar Hashiva, Israel.

Asexual reproduction of the new cultivar 'DGAUDARIP' was first performed by terminal vegetative cuttings during November of 2019, at a greenhouse in Moshav Mishmar Hashiva, Israel. Subsequent propagation by has shown that the unique features of this cultivar are stable and reproduced true to type in successive generations.

SUMMARY OF THE INVENTION

The cultivar 'DGAUDARIP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DGAUDARIP'. These characteristics in combination distinguish 'DGAUDARIP' as a new and distinct *Gaura* cultivar:

1. Very good branching.
2. Abundant flower coverage.

3. Semi-upright habit.
4. Compact-medium sized plant.
5. Early flowering.

PARENT COMPARISONS

Plants of the new cultivar 'DGAUDARIP' are similar to plants of the seed parent in most horticultural characteristics, however, plants of the new cultivar 'DGAUDARIP' differ in the following;

1. The new cultivar has pink flowers, while the seed parent has white flowers.
2. The new cultivar has a more compact habit than the seed parent.
3. The new cultivar has darker foliage than the seed parent.
4. The new cultivar has shorter stems than the seed parent.

Plants of the new cultivar 'DGAUDARIP' are similar to plants of the pollen parent in most horticultural characteristics however, plants of the new cultivar 'DGAUDARIP' differ in the following;

1. The new cultivar flowers earlier than the pollen parent.

COMMERCIAL COMPARISON

Plants of the new cultivar 'DGAUDARIP' can be compared to the patented commercial cultivar *Gaura* 'BELLEZA Dark Pink', unpatented. These varieties are similar in most horticultural characteristics; however, 'DGAUDARIP' differs in the following:

1. Flowers of the new cultivar are brighter pink than flowers of this comparator.
2. The new cultivar has shorter stems than this comparator.

Plants of the new cultivar 'DGAUDARIP' can be compared to the patented commercial cultivar *Gaura* 'Gambit Rose', unpatented. These varieties are similar in most horticultural characteristics; however, 'DGAUDARIP' differs in the following:

1. The new cultivar flowers earlier than this comparator.
2. The new cultivar has a more uniform, less spreading habit than this comparator.
3. The new cultivar produces more flowers than this comparator.

BRIEF DESCRIPTION OF THE PHOTOGRAPHS

The accompanying photograph in FIG. 1 illustrates in full color a typical plant in a 20 cm pot, at approximately 5 months of age, of 'DGAUDARIP' grown in a greenhouse, in Moshav Mishmar Hashiva, Israel.

Figure 2:
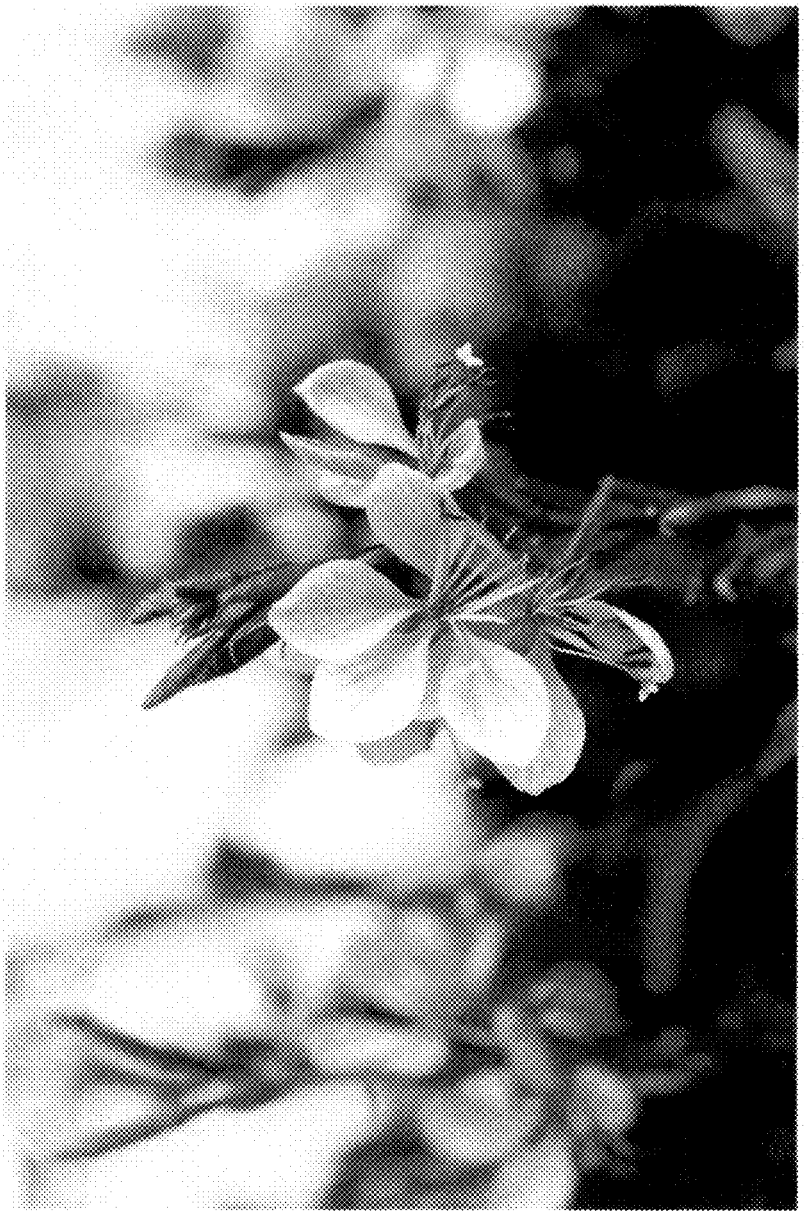

FIG. 2 illustrates in full color typical flowers of the new cultivar.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DGAUDARIP' plants grown in greenhouse in Moshav Mishmar Hashiva, Israel, under natural lighting. The plants were approximately 5 weeks old from a rooted cutting. The growing temperature ranged from 18° C. to 37° C. during the days, to 15° C. to 22° C. during the nights. Measurements and numerical values represent averages of typical plant types.

Botanical classification: *Gaura lindheimeri* 'DGAUDARIP'

PROPAGATION

Time to rooting: 14 days at approximately 16-20° C.
Time to produce a rooted plantlet: About 20 days.
Root description: Fibrous, colored near RHS White 155D.

PLANT

Growth habit: Semi-upright, compact.
Height: 27 cm.
Plant spread: Approximately 18 cm.
Growth rate: Medium.
Length of primary lateral branches: Approximately 24 cm.
Diameter of lateral branches: Approximately 0.3 cm.
Quantity of primary lateral branches: Average 6.
Characteristics of primary lateral branches:
- *Form*.—Round, pubescent.
- *Color*.—Immature branches: Upper tip close to RHS Red-Purple 59B. Bellow: Close to RHS Green 137B. Mature branches: Close to RHS Green 137C.
- *Texture*.—Glabrous.
- *Strength*.—Strong, somewhat flexible.

Internode length.—1.5 cm; about 2 cm at the tip.

FOLIAGE

Leaf:
- *Arrangement*.—Alternate, simple.
- *Quantity*.—Approximately 15 to 20 fully developed per branch.
- *Average Length*.—4.5 to 6 cm.
- *Average width*.—1 to 1.4 cm.
- *Shape of blade*.—Oblanceolate.
- *Apex*.—Acute.
- *Base*.—Cuneate.
- *Margin*.—Entire.
- *Texture of top surface*.—Mostly glabrous.
- *Texture of bottom surface*.—Scant pubescence.
- *Aspect*.—Flat with little undulation at apex.
- *Color*.—Young Foliage, Upper Side: Near RHS Green 137A. Young Foliage, Under Side: Near RHS Green 137B. Mature Foliage, Upper Side: Near RHS Green N137B. Mature Foliage, Under Side: Near RHS Green N137D.
- *Venation*.—Type: Pinnate. Color: Mature Foliage, Upper Side: Near RHS Yellow-Green 193A. Mature Foliage, Under Side: Near RHS Yellow-Green 193C. Young Foliage, Upper Side: Near RHS Yellow-Green 193A. Young Foliage, Under Side: Near RHS Yellow-Green 193B.
- *Petiole*.—Sessile.

FLOWER

Natural flowering season: Spring through summer.
Inflorescence and flower type and habit: Single zygomorphic flowers produced on terminal and axillary racemes.
Persistence: Self-cleaning.
Fragrance: None.
Bud:
- *Shape*.—Oblong.
- *Length*.—1.1 to 1.6 cm.
- *Diameter*.—0.2 cm.
- *Color*.—Near RHS Purple-Red 60C; tip near Green 137B.

Raceme:
- *Diameter*.—Average 5 cm.
- *Length*.—Average 12 cm.
- *Flowers per raceme*.—About 10 (5 open flowers).
- *Flower size*.—Diameter/Width: Average 3.3 cm. Length: Average 2 cm.

Corolla/petals:
- *Quantity of petals*.—4.
- *Arrangement*.—Symmetrical whorl.
- *Petal length*.—1.6 cm. Petal Width: Approximately 0.7 cm. Corolla Tube Length: 1.1 cm. Corolla Tube Diameter: 0.1 cm. Texture: Glabrous. Petal Apex: Rounded (obtuse). Petal Base: Pointed (acute).
- *Petal shape*.—Rounded, spatulate. Margin: Entire. Aspect: Upwardly cupped.
- *Petal color*.—When Opening: Upper Surface: Near RHS Purple-Red 64C. Lower Surface: Near RHS Purple-Red 64C. Fully Opened: Upper Surface: Near RHS Purple-Red N66C; veins 64C. Lower Surface: Near RHS Purple-Red N66C; veins 64C. Fading: Upper Surface: Near RHS Purple-Red 65C; veins N66D. Lower Surface: Near RHS Purple-Red 65C; veins N66D.

*Outer corolla tube color*.—Near RHS Purple-Red 61B.

*Inner corolla tube color*.—Near RHS Yellow-Green 144A and Purple-Red 63C.

Calyx/sepals:

*Quantity per flower*.—4. Shape: Linear. Length: 1.9 cm. Width: 0.2 cm. Apex: Acute. Base: Truncate. Margin: Entire. Texture: Glabrous. Aspect: Undulating and strongly reflexed back.

*Color*.—Upper Surface: Near RHS Purple-Red 58A. Lower Surface: Near RHS Purple-Red 58A.

Peduncle:

*Length*.—Average 2.5 to 3 cm. Diameter: Approximately 0.15 cm. Color: Near RHS Green 137C. Orientation: Straight, approximately 20° angle from stem. Texture: Glabrous. Strength: Strong.

Pedicel: Not present, directly attached by corolla tube to peduncle.

Fragrance: Not observed.

REPRODUCTIVE ORGANS

Stamens:

*Number*.—8.

*Filament length*.—About 1.5 cm.

Anthers:

*Length*.—Approximately 0.3 cm.

*Shape*.—Linear.

*Color*.—Near RHS Purple-Red 59A.

*Pollen*.—Color: Near RHS Yellow 1C. Quantity: Plenty.

Pistil:

*Number*.—1.

*Length*.—1.8 cm.

*Style*.—Length: 1.7 cm. Color: Near RHS Purple-Red 59C.

*Stigma*.—Shape: 4-lobed. Color: Near RHS White N155D. Ovary Color: Near RHS Purple-Red 59A. Ovary Length: Approximately 0.8 cm. Ovary Diameter: Approximately 0.15 cm. Ovary Shape: Linear.

OTHER CHARACTERISTICS

Seeds and fruits: Not observed to date.

Disease/pest resistance: Typical to known *Gaura* varieties. Neither resistance nor susceptibility to the normal diseases and pests of *Gaura* have been observed.

Temperature tolerance: 10° C. to 38° C.

What is claimed is:

1. A new and distinct cultivar of *Gaura* plant named 'DGAUDARIP' as herein illustrated and described.

* * * * *